United States Patent
Augarten et al.

(10) Patent No.: US 12,377,183 B2
(45) Date of Patent: Aug. 5, 2025

(54) COUNTING UNIT

(71) Applicant: KARL STORZ Imaging, Inc., Goleta, CA (US)

(72) Inventors: Michael Augarten, Goleta, CA (US); Edward Schifferns, Santa Barbara, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 735 days.

(21) Appl. No.: 17/652,651

(22) Filed: Feb. 25, 2022

(65) Prior Publication Data
US 2023/0270906 A1 Aug. 31, 2023

(51) Int. Cl.
*G01K 1/02* (2021.01)
*A61L 2/07* (2006.01)
*A61L 2/26* (2006.01)
*G06C 27/00* (2006.01)
*G11C 19/00* (2006.01)

(52) U.S. Cl.
CPC .................. *A61L 2/26* (2013.01); *A61L 2/07* (2013.01); *A61L 2202/14* (2013.01)

(58) Field of Classification Search
CPC ....... G06M 1/00; G06K 19/0723; G01K 1/02; G06C 27/00
USPC .................... 377/25, 65; 235/103, 91 R, 116
See application file for complete search history.

(56) References Cited

U.S. PATENT DOCUMENTS

| | | |
|---|---|---|
| 4,382,063 A | 5/1983 | Romito |
| 5,143,453 A | 9/1992 | Weynant née Girones |
| 5,174,300 A | 12/1992 | Bales |
| 5,313,935 A | 5/1994 | Kortenbach et al. |
| 5,359,993 A | 11/1994 | Slater |
| 5,452,335 A | 9/1995 | Slater et al. |
| 5,969,315 A | 10/1999 | Schulze |
| 6,166,538 A | 12/2000 | D'Alfonso |
| 6,736,085 B1 | 5/2004 | Esnouf |
| 6,837,620 B2 | 1/2005 | Shahinpoor |
| 8,172,458 B2 | 5/2012 | Petrakis |
| 2005/0105587 A1 | 5/2005 | Shahinpoor |
| 2019/0236435 A1* | 8/2019 | Spieth ................ G06K 19/0723 |

FOREIGN PATENT DOCUMENTS

DE 102005054546 A1 5/2007

OTHER PUBLICATIONS

Geiger, H.-W., Extended European Search Report, Jun. 19, 2003, pp. 1-7, European Patent Office, Munich.

* cited by examiner

*Primary Examiner* — Monzer R Chorbaji
(74) *Attorney, Agent, or Firm* — David N. Villalpando; Jacqueline Cohen

(57) ABSTRACT

A counting unit is provided for use in an electrical device. The counting unit is configured to count a thermal event such as an autoclave cleaning operation when the electrical device is not electrically powered. In one aspect, the counting unit includes a rotary member and an actuator, the actuator is configured to change shape from a first configuration to a second configuration when subjected to a predetermined temperature, wherein in the second configuration, the actuator engages the rotary member so as to rotate the rotary member. In another aspect, the counting unit includes a plunger, a drive and a heat resistant arm configured to release the plunger during a thermal event and retain the plunger when the electrical device is cooled down.

17 Claims, 5 Drawing Sheets

COUNTING UNIT

The present disclosure relates generally to the field of a counting unit for counting a thermal event.

BACKGROUND

Electrical devices may require sterilization. A current sterilization process is autoclaving, which subjects the electrical device to high temperature and pressure sufficient to kill germs, bacteria and viruses. As such, the electrical devices cannot be powered during the sterilization process. However, it is desirable to count the number of times the electrical device has been sterilized so as to determine when maintenance is required.

As such, it is desirable to have a counting device which can count the number of times an electrical device is sterilized without requiring electrical power during the sterilization process.

SUMMARY

In a first embodiment of the disclosure, a counting unit for counting a number of times an electrical device has been sterilized is provided. The counting unit includes a rotary member, an actuator and a sensor. The rotary member is configured to rotate about a first axis, the rotary member includes a plurality of position indicators fixedly disposed on the rotary member. The actuator is configured to engage the rotary member. The actuator is further configured to change shape from a first configuration to a second configuration when subjected to a predetermined temperature. In the second configuration, the actuator engages the rotary member so as to rotate the rotary member. The sensor is configured to detect the position indicators so as to determine a rotation of the rotary member.

In one aspect of the counting unit, the rotary member includes a plurality of teeth. In such an aspect, the actuator is configured to engage one of the plurality of teeth in the second configuration so as to rotate the rotary member in a first direction.

In another aspect of the counting unit, the counting unit further includes a catch. The catch is rotatable about a second axis and configured to engage one of the plurality of teeth so as to prevent the rotary member from rotating in a second direction, the second direction opposite of the first direction.

In another aspect of the counting unit, the counting unit further includes a biasing member configured to continuously urge the rotary member in the second direction.

In yet another aspect of the counting unit, the actuator is an elongated member having a proximal end and a distal end. The distal end is configured to engage one of the plurality of teeth. In the first configuration a distance between the proximal end and the distal end is a first length and in the second configuration the distance between the proximal end and the distal end is a second length. A distance between the distal end of the first length and the distal end of the second length is greater than a distance from one of the plurality of teeth to an adjacent one of the plurality of teeth.

In one aspect, the actuator is an elongated member made of a shape memory alloy. The shape memory alloy may be made from one of a copper-aluminum-nickel alloy and a nickel titanium alloy.

In a second embodiment of the disclosure, the actuator is a wound member configured to radially expand when subjected to the predetermined temperature. In such an aspect, the wound member is made of a bimetallic material.

In a third embodiment of the disclosure, a counting unit includes a housing, a plunger, a heat responsive arm, a drive, a sensor, and a controller. The plunger is disposed within the housing. The plunger includes a catch and is moveable from a seated position to an extended position. The second biasing member is disposed within the housing. The second biasing member continuously urges the plunger out of the housing. The heat responsive arm is movable from an engaged position and a disengaged position, wherein the heat responsive arm is moved to the disengaged position when the heat responsive arm reaches a predetermined temperature, and wherein the heat responsive arm is in the engaged position when the heat responsive arm is below the predetermined temperature. In the engaged position, the heat responsive arm locks the plunger in the seated position. In the disengaged position, the heat responsive arm is disengaged with the plunger. The drive is electrically powered. The drive is operable to move the plunger from the extended position to the seated position. The sensor is configured to detect the plunger when the plunger is in the extended position. The controller is configured to detect and count the number of times the drive moves the plunger from the extended position to the seated position.

In yet another aspect of the third embodiment, the drive is a coil of wire. The heat responsive arm is formed of a bimetallic material. In another aspect, the counting unit further includes a power input configured to provide electrical power to the drive so as to move the plunger into the extended position when connected to electric power.

BRIEF DESCRIPTION OF THE DRAWINGS

The embodiments set forth in the drawings are illustrative and exemplary in nature and not intended to limit the subject matter defined by the claims. The following description of the illustrative embodiments can be understood when read in conjunction with the following drawings, where like structure is indicated with like reference numerals and in which:

DETAILED DESCRIPTION

In one aspect of the disclosure, a counting unit is provided for use in an electrical device. The counting unit is configured to count a thermal event such as an autoclave cleaning operation when the electrical device is not electrically powered. In one aspect, the counting unit includes a rotary member and an actuator, the actuator is configured to change shape from a first configuration to a second configuration when subjected to a predetermined temperature, wherein in the second configuration, the actuator engages the rotary member so as to rotate the rotary member. A sensor is configured to detect a rotation of the rotary member so as to detect a thermal event.

In another aspect, the counting unit includes a plunger and a biasing member configured to continuously urge the plunger in an extended position and a drive configured to overcome the force of the biasing member so as to move the plunger in a seated position. A heat responsive arm is movable from an engaged position and a disengaged position, wherein the heat responsive arm is moved to the disengaged position when the heat responsive arm reaches a predetermined temperature and the heat responsive arm is in the engaged position when the heat responsive arm is below the predetermined temperature. In the engaged position the heat responsive arm locks the plunger in the seated position and in the disengaged position, the heat responsive arm is disengaged with the plunger. As such, when a heating event occurs the plunger is placed in the extended position and moved to the retracted position when the drive is powered.

Figure 1:
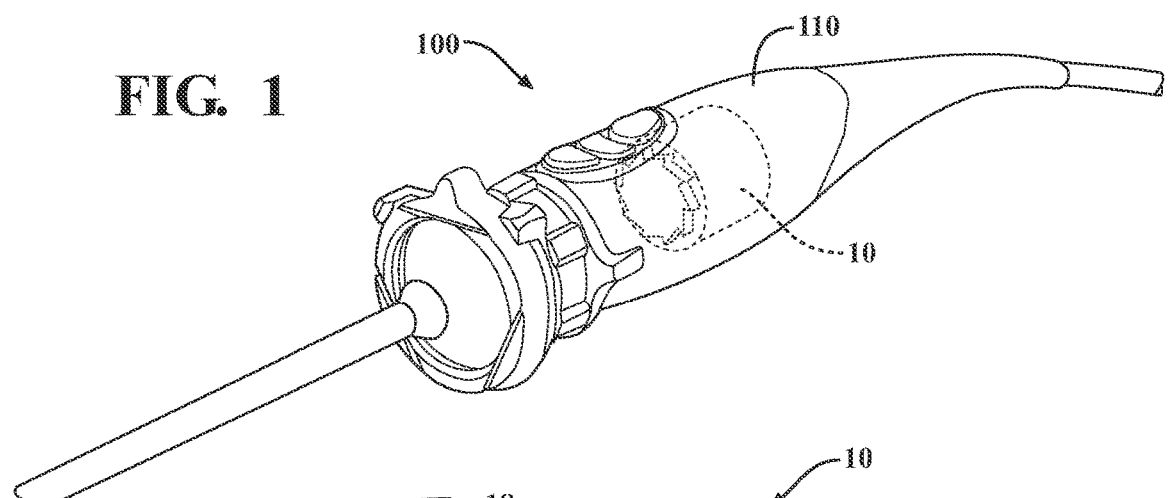
FIG. 1 is a perspective view of an illustrative depiction of an electrical device having a counting unit according to the embodiments described herein.

With reference first to FIG. 1, an exemplary depiction of an electrical device 100 is provided. The electrical device 100 includes a counting unit 10 configured to count a thermal event. For illustrative purposes, the electrical device 100 will be described in the context of an endoscope.

The endoscope is sterilized by an autoclave, wherein pressurized steam is directed onto the endoscope. As used herein, a thermal event means any process in which the electrical device 100 is subjected to heat, to include autoclaving. Further, it should be appreciated that the counting unit 10 described herein may be applicable to any electrical device 100 subject to a thermal event. The electrical device 100 includes a housing 110 configured to house electric components for performing an intended use. The counting unit 10 is disposed within the housing 110. FIG. 1 shows a generic depiction of the counting unit 10, while FIGS. 2-12 provide a detailed illustration of the counting unit 10.

With reference now to FIGS. 2-5, a depiction of a first embodiment of a counting unit 10 is provided. The counting unit 10 is configured to count the number of times the electrical device 100 has been subjected to a thermal event, such a sterilization within an autoclave.

The counting unit 10 includes a rotary member 12, an actuator 14 and a first sensor 16. The rotary member 12 is a gear having a plurality of teeth 18 disposed on the circumference of the rotary member 12. The rotary member 12 is rotatable about a fixed pin 20 which is fixed to a substrate 22 which may be formed within the housing 110. The fixed pin 20 defines a first axis of the rotary member 12. The first axis is generally centered with respect to the rotary member 12. Preferably, the rotary member 12 is configured to freely rotate in a clockwise and counter-clockwise direction. The rotary member 12 is illustratively shown as having ten teeth 18. It should be appreciated that the number of teeth 18 depicted is illustrative and not limiting to the scope of the appended claims.

Figure 4:
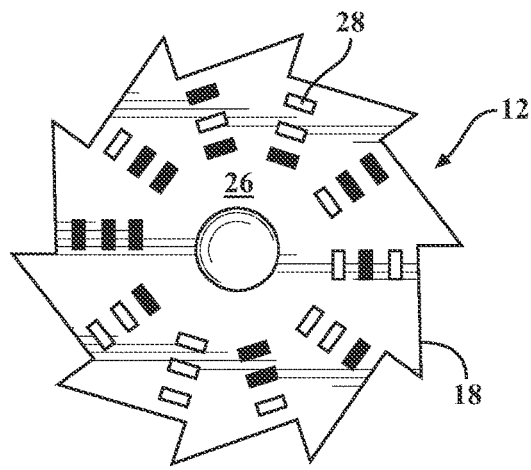
FIG. 4 is an isolated view of a back side of the rotary member in FIGS. 2 and 3 showing the position indicators.

The rotary member 12 includes a first surface 24 opposite of a second surface 26. The second surface 26 faces the substrate 22. Preferably, the first and the second surfaces 24, 26 are generally planar. The rotary member 12 further includes a plurality of position indicators 28 fixedly disposed on the second surface 26 of the rotary member 12. A depiction of the position indicators 28 is illustratively shown in FIG. 4. FIG. 4 depicts the position indicators 28 as binary encoding printed on the second surface 26, wherein the binary codes of the binary encoding may be metallic traces. The rotary member 12 is shown as having a position indicator 28 associated with each teeth 18. The binary codes are patterned so as to indicate a position associated with a respective teeth 18. In one aspect, the binary codes are patterned in such a manner that the number of metallic traces is different with respect to adjacent binary codes on respective teeth 18.

With reference again to FIGS. 4 and 5, the first sensor 16 is opposite of and faces the second surface 26 of the rotary member 12. The first sensor 16 is a printed circuit board 30 having a microcontroller 32 and a plurality of conductive traces 34 electrically connected to the microcontroller 32 on one end and a contact pad 36 on the other. The contact pads 36 may be formed of an electrically conductive material configured to complete an electric connection with a corresponding metallic trace or binary encodes of the position indicator 28.

Figure 5:
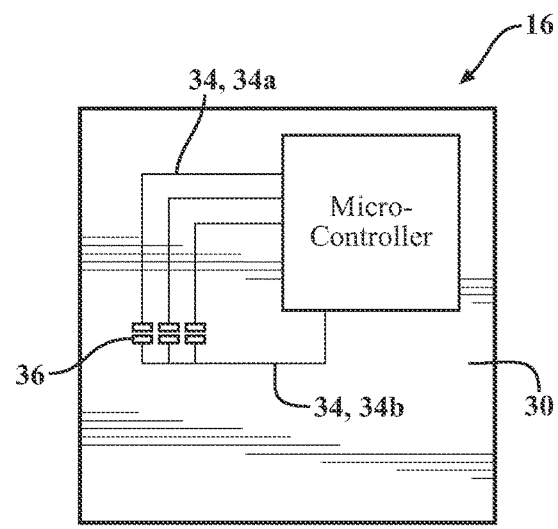
FIG. 5 is a top down view of a sensor for use in the counting unit shown in FIGS. 2 and 3.

In the depiction shown in FIGS. 4 and 5, the printed circuit board 30 includes three conductive traces 34 defining an output path 34a for a control signal from the microcontroller 32 and three conductive traces 34 defining an input path 34b for a position signal. In this case, an electrical connection made between the contact pad 36 and the metallic trace of the binary encoded rotary member 12 is processed to determine if there is a change in a position of the rotary member 12.

With reference again to FIGS. 2 and 3, an illustrative depiction of the actuator 14 is provided. The actuator 14 is configured to engage the rotary member 12. In particular, the actuator 14 is configured to engage the rotary member 12 by changing shape from a first configuration to a second configuration when subjected to a predetermined temperature. In the first configuration, the actuator 14 is bent as shown in a solid line in FIG. 3. When heated to a predetermined temperature, the actuator 14 changes shape to the second configuration, wherein the actuator 14 straightens out as shown in dashed lines in FIG. 3 (also shown in a solid line in FIG. 2). As shown in FIG. 3, as the actuator 14 changes from the first configuration (i.e., bent) to the second configuration (i.e., straight), a distal end of the actuator 14 presses the corresponding tooth 18 so as to rotate the rotary member 12. In particular, the actuator 14 rotates the rotary member 12 in a first direction, which is a counter-clockwise direction as indicated by the arrow in FIGS. 2 and 3.

In one aspect, the counting unit 10 may further include a first catch 38. The first catch 38 is rotatable about second pin 40 which defines a second axis. The second pin 40 may be fixed to the substrate 22 and is configured to engage one of the plurality of teeth 18 so as to prevent the rotary member 12 from rotating in a second direction, the second direction is opposite of the first direction. In this case, the second direction is a clockwise direction.

Figure 2:
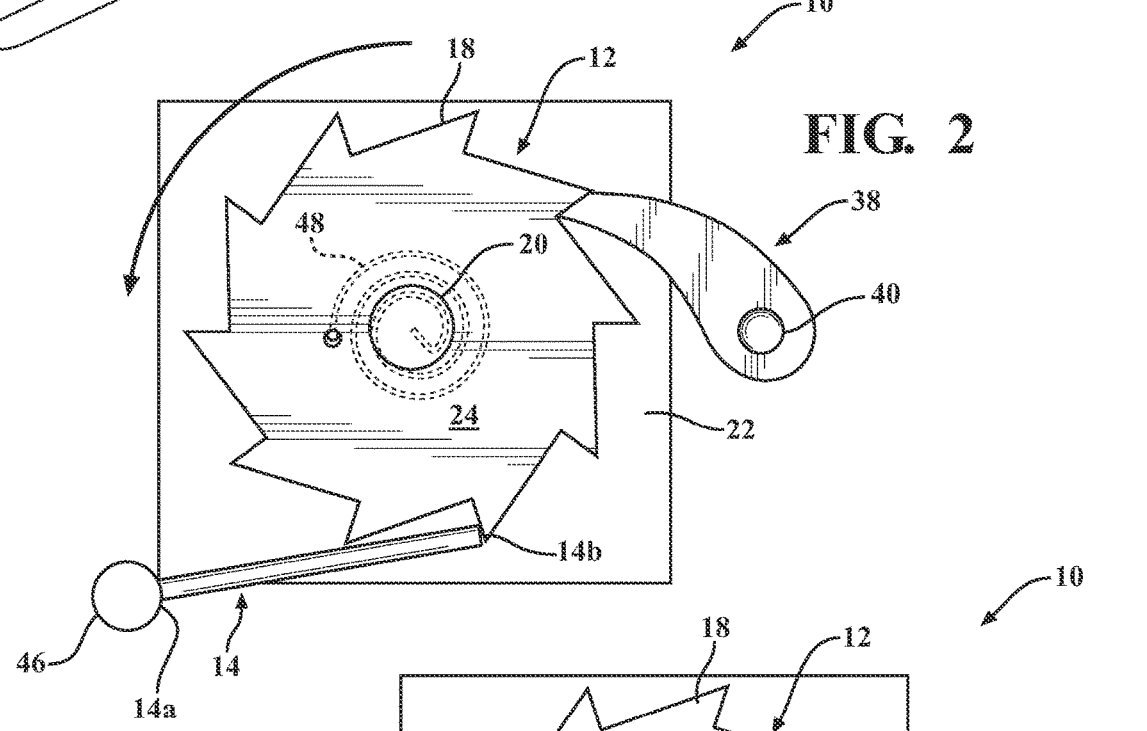
FIG. 2 is a top down view of a first embodiment of a counting unit configured for use in the electric device shown in FIG. 1.
Figure 3:
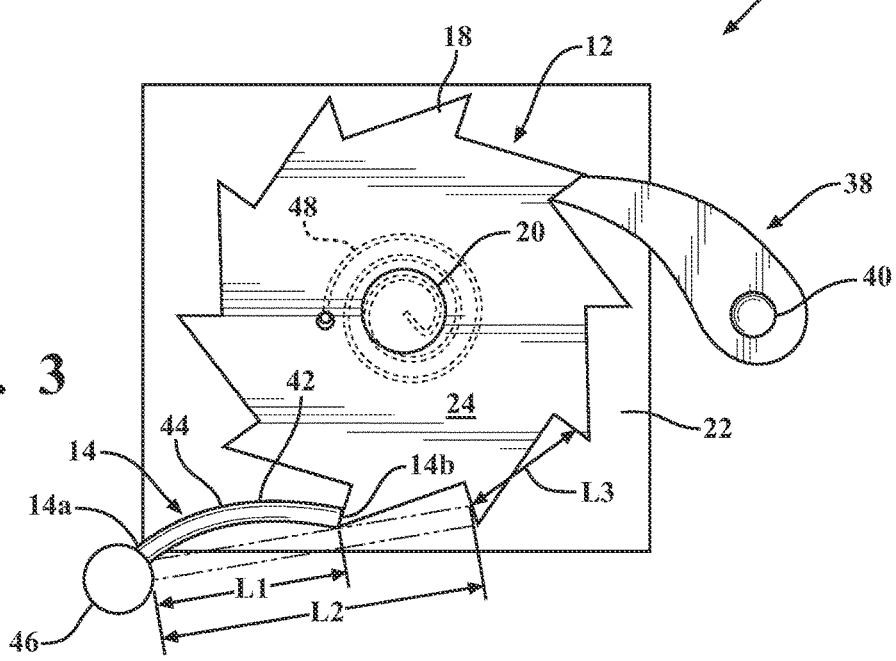
FIG. 3 is a top down view the counting unit in FIG. 2 showing the actuator changing shape from a first configuration to a second configuration.

FIGS. 2 and 3 depict the actuator 14 as being an elongated member having a proximal end 14a and a distal end 14b. The proximal end 14a is fixed to the substrate 22. The distal end 14b is configured to engage one of the plurality of teeth 18. In the first configuration a distance between the proximal end and the distal end is a first length "L1" as indicated in FIG. 3. In the second configuration the distance between the proximal end and the distal end is a second length "L2" which is commensurate with the length of the actuator 14. A distance between the distal end of the first length "L1" and the distal end of the second length "L2" is greater than a distance "L3" between adjacent teeth 18. Thus, as the actuator 14 changes shape from the first configuration to the second configuration, the degree of rotation is sufficient to rotate rotary member 12 wherein the teeth 18 advance sufficiently to allow the first catch 38 to engaging a preceding tooth 18.

As discussed above, the actuator 14 is an elongated member. A proximal end of the main body portion 42 may be fixed to an anchor point 46. It should be appreciated that the actuator 14 is formed of a material configured to change shape when subjected to a predetermined temperature. As an example, the actuator 14 may be formed of a shape memory alloy. The shape memory alloy may be made from one of a copper-aluminum-nickel alloy and a nickel titanium alloy. Such material may be tuned to change shape when subjected to a predetermined temperature. The process of making such a material with the desired shape changing functions is currently known and used and may be modified for use herein. The actuator 14 may be described as having a main body portion 42 and a flex portion 44. The flex portion 44 is contiguous with the main body portion 42 and is illustratively shown as being generally centered within the main body portion 42. However, it should be appreciated that the flex portion 44 may be disposed in other regions of the main body 42, such as a distal end or a proximal end of the main body so long as the actuator 14 engages the rotary member 12 when the actuator 14 changes from a first configuration to a second configuration. In the illustrative example of an actuator being an elongated member, the flex portion 44 is operable to straighten the main body portion 42 when the actuator 14 is subjected to the predetermined temperature and concurrently rotating the rotary member 12.

The counting unit 10 may further include a first biasing member 48. The first biasing member 48 is configured to continuously urge the rotary member 12 in the second direction. Thus, the first biasing member 48 is configured to cooperate with the first catch 38 to retain a corresponding tooth 18 in engagement with the first catch 38 and keep the rotary member 12 from rotating.

In operation, as the electrical device 100 is subject to a thermal event such as autoclaving. It should be appreciated that prior to autoclaving, the actuator is at room temperature and thus is bent, as shown in solid line in FIG. 3. During autoclaving, the actuator 14 is subjected to a temperature sufficient to actuate the actuator 14 so as to change shape from the first configuration to the second configuration, as shown in FIG. 2 and in dashed lines in FIG. 3. Specifically, the actuator 14 straightens out so as to push against a corresponding tooth 18 of the rotary member 12. The force of the actuator 14 as it straightens out is enough to overcome the opposing force of the first biasing member 48 so as to rotate the rotary member 12 in the first direction (counter-clockwise).

The actuator 14 is formed of a shape memory alloy having a resiliency sufficient to overcome the force of the first biasing member 48. Preferably the actuator 14 is bent in the first configuration and is straight in the second configuration wherein the distal end 14b of the actuator 14 travels a distance, the difference between "L1" and "L2", which is greater than the distance "L3" between adjacent teeth 18. Simultaneously, the teeth 18 engaged with the first catch 38 rotates away from the first catch 38, and the first catch 38 slides against an angled surface of the preceding tooth 18 and passes the preceding tooth 18 so as to fall onto the angled surface of the next tooth 18. The first biasing member 48 urges the rotary member 12 in the second direction, placing the first catch 38 into engagement with the preceding tooth 18 so as to fix the rotary member 12 in position. During this process, the position indicators 28 are moved, wherein the preceding position indicator 28 is placed into contact with the contact pads 36 of the first sensor 16.

When the electrical device 100 is removed from the autoclave or allowed to cool down, the actuator 14 is returned to the first configuration so as to move into a position to engage a preceding tooth 18. When the electrical device 100 is powered, the first sensor 16 is powered and the microcontroller 32 is able to read the position indicator 28 and compare the reading from the position indicator 28 of a previous unpowered state to determine if the position of the rotary member 12 has changed. This may be accomplished by simply comparing if the position indicator 28 value has changed. Thus, a change in position may be determined by having the position indicators 28 alternating in patterns between each other. That is, the binary encoding pattern may simply be two different patterns, as opposed to the seven different patterns shown in FIG. 4.

The microcontroller 32 may be further programmed to associate that change in position with a thermal event and thereby associate the change in position with a thermal event, or a sterilization. Accordingly, the counting unit 10 is able to count the number of times the electrical device 100 has been sterilized. It should be appreciated that the microcontroller may be disposed within the electrical device 100 or may be disposed on a camera control unit (not shown), but the contact pads 36 are positioned so as to read the position indicators 28. Thus, the printed circuit board 30 may simply include the conductive traces 34 which are electrically connected to the microcontroller 32 which is disposed in the camera control unit.

Figure 6:
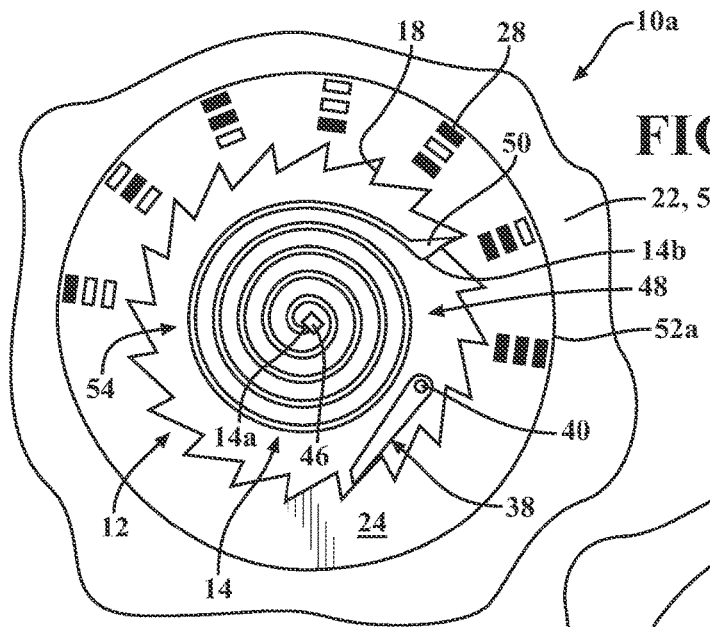
FIG. 6 is a top down view of a second embodiment of a counting unit configured for use in the electric device shown in FIG. 1.
Figure 7:
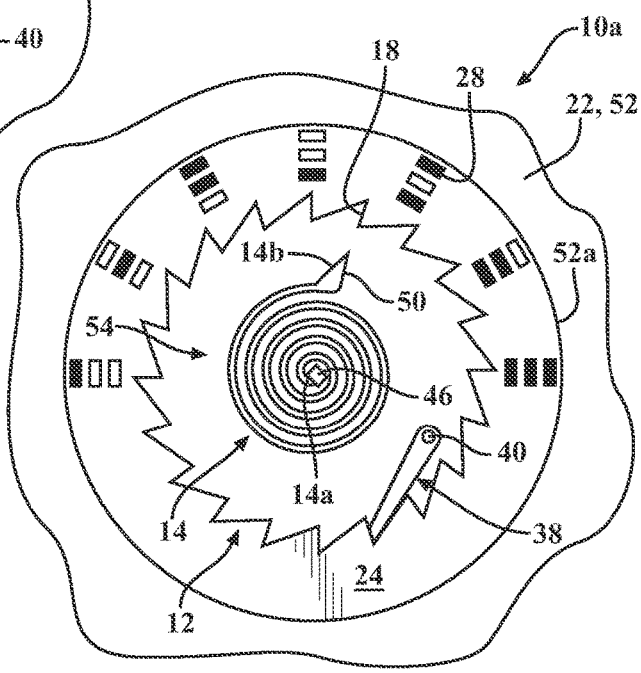
FIG. 7 is a view of the counting unit shown in FIG. 6 wherein the actuator is not actuated.

With reference now to FIGS. 6 and 7, a second embodiment of a counting unit 10a is provided. As shown, the actuator 14 is a wound member configured to radially expand when subjected to the predetermined temperature. In such an aspect, the wound member is made of a bimetallic material. The proximal end 14a of actuator 14 is fixedly disposed to an anchor point 46 within the rotary member 12. The anchor point 46 is centered within the rotary member 12 so as to be generally centered within the rotary member 12. The distal end 14b of the actuator 14 includes an engagement member 50. The engagement member 50 includes a flat surface for engaging the teeth 18.

The rotary member 12 is freely rotatable in a clockwise and counter-clockwise direction. The rotary member 12 may be held in a carrier 52 which has a circular pocket 52a allowing the rotary member 12 to rotate therein. The carrier 52 may be integrated into the housing 110 of the electrical device 100. As shown in FIGS. 6 and 7, the teeth 18 are disposed within a circular opening 54 of the rotary member 12, as is the first catch 38, and the rotary member 12 is centered within the circular opening 54. The position indicators 28 are disposed on the first surface 24 of the rotary member 12.

As with the first embodiment, the actuator 14 is configured to rotate the rotary member 12 when the actuator 14 (also referred to as a wound member 14) changes shape from a first configuration to a second configuration. In the first configuration (shown in FIG. 7), the wound member 14 is contracted, while in the second configuration (shown in FIG. 6), the wound member 14 is expanded. The wound member 14 radially expands from the first configuration to the second configuration when subjected to a thermal event, such as a sterilization within an autoclave. As the wound member 14 expands radially, the distal end 14b of the wound member 14 moves further from the center of the wound member 14 in a radial direction and engages a tooth 18, rotating the rotary member 12 in a clockwise direction.

It should be appreciated that the wound member 14 is configured to rotate the rotary member 12 a distance greater than a distance between adjacent teeth 18. A first biasing member 48 (not shown) may be disposed on the second surface 26 of the rotary member 12 which is formed on an opposite side of the first surface 24 of the rotary member 12 which is shown in FIGS. 6 and 7. As with the first embodiment, the first biasing member 48 is configured to urge the rotary member 12 in a counter-clockwise direction, placing the first catch 38 into engagement with a tooth 18. As with the first embodiment, the rotation of the rotary member 12 rotates the position indicators 28. The first sensor 16 shown in FIG. 5 may be adapted and modified for use in the second embodiment. As such, the printed circuit board 30 is positioned over the first surface 24, and processes a change in position in the same manner as described above. For example, the first sensor 16 is placed on top of the first surface 24 of the rotary member 12 so as to position the contact pads 36 above the position indicators 28.

An operation of the counting unit 10a according to the second embodiment is now provided. As the electrical device 100 is subject to a thermal event, the distal end 14b including the engagement member 50 of the wound member 14 expands radially and engages one of the teeth 18 of the rotary member 12 and rotates the rotary member 12 so as to advance the tooth 18 a distance greater than the distance between adjacent teeth 18, thus the position indicators 28 are also advanced, wherein a preceding position indicator 28 is now positioned opposite of the contact pad 36 of the first sensor 16.

When the electrical device 100 is removed from the autoclave or allowed to cool down, the actuator 14 is returned to the first configuration wherein the distal end 14b including the engagement member 50 of the wound member 14 is spaced apart from the teeth 18, as shown in FIG. 7. When the electrical device 100 is powered, the first sensor 16 is powered and the microcontroller 32 is able to read the position indicator 28 and compare the reading from the position indicator 28 to determine that the position of the rotary member 12 has changed. The microcontroller 32 may be further programmed to associate that change in position with a thermal event and thereby associate the change in position with a thermal event, or a sterilization. Accordingly, the counting unit 10a is able to count the number of times the electrical device 100 has been sterilized.

Figure 8:
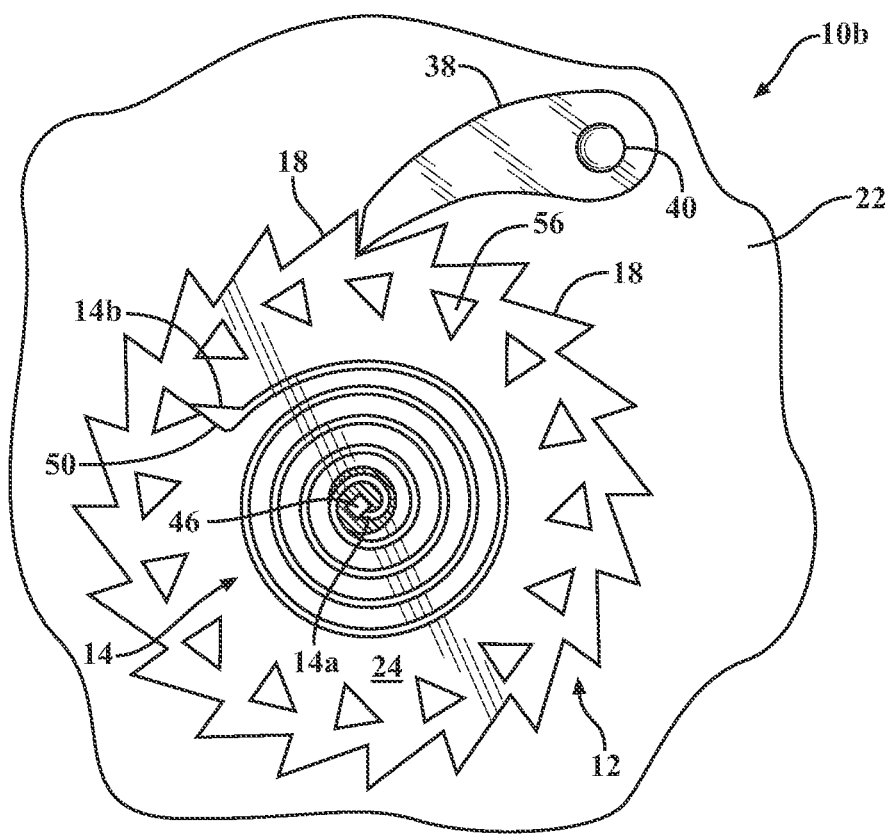
FIG. 8 is a top down view of a second aspect of the counting unit shown in FIGS. 6 and 7, showing the actuator in an expanded state.
Figure 9:
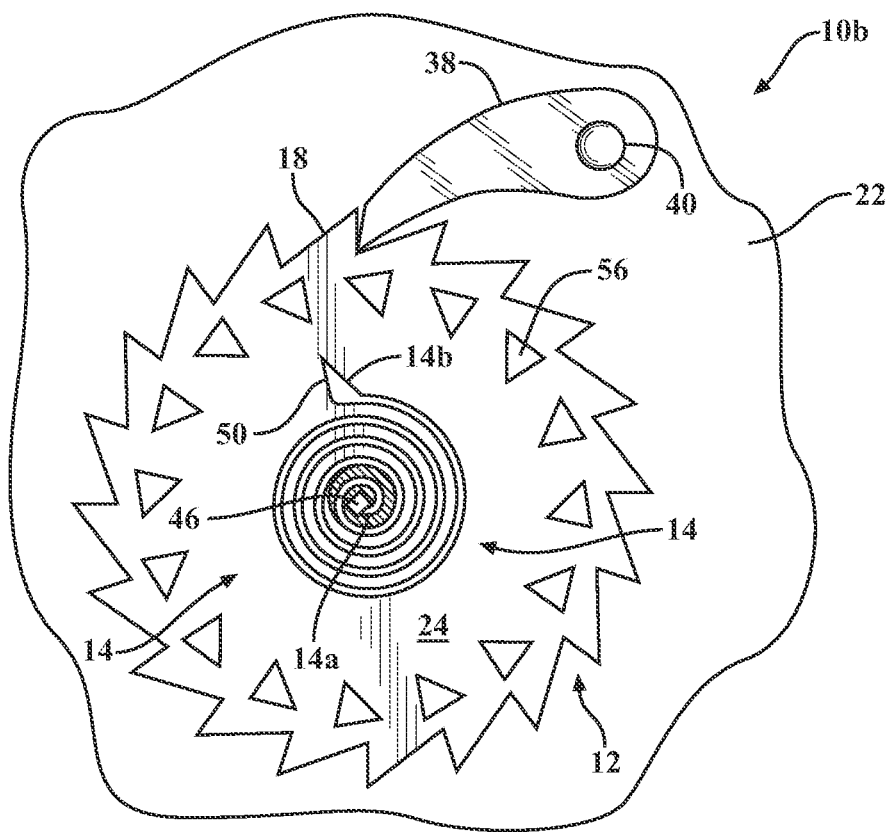
FIG. 9 is a view of the counting unit shown in FIG. 8, wherein the actuator is not actuated.
Figure 10:
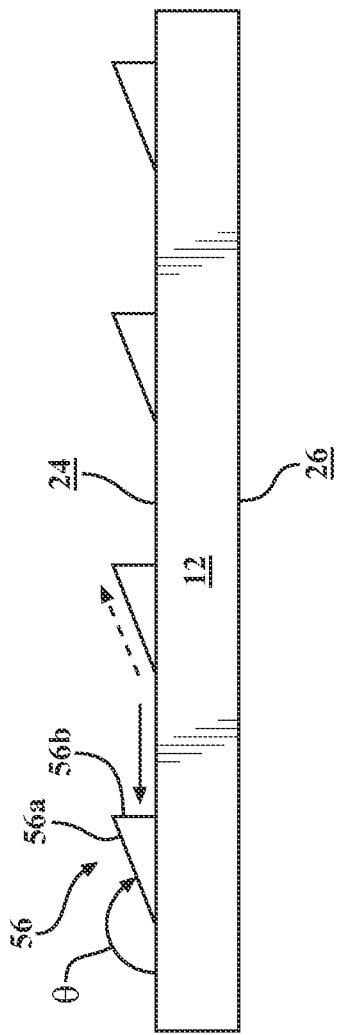
FIG. 10 is a cross-sectional view of the rotary member shown in FIGS. 8 and 10.

With reference now to FIGS. 8-10, another aspect of the second embodiment of the counting unit 10b is provided. The processing of the position indicators 28 and thus the counting of a thermal event is the same as described above; however, the mechanical operation of the actuator 14 with respect to the rotary member 12 is different.

As shown in FIGS. 8-10, the actuator 14 is a wound member 14. The wound member 14 may be the same as the wound member 14 disclosed in FIGS. 6 and 7. Specifically, the wound member 14 moves between the first configuration (shown in FIG. 9) where the wound member 14 is contracted, and the second configuration (shown in FIG. 8) where the wound member 14 is expanded. The actuator 14 is mounted on the first surface 24 of the rotary member 12. The rotary member 12 includes a plurality of teeth 18 disposed on the circumference of the rotary member 12. The rotary member 12 further includes a plurality of ramps 56 disposed on the first surface 24 of the rotary member 12. As shown in FIG. 10, the ramps 56 have a top surface 56a which is angled and a front surface 56b which is generally orthogonal to the first surface 24 of the rotary member 12. The top surface 56a is angled so as to form an obtuse angle "θ" with respect to the first surface 24 as indicated in FIG. 10. Accordingly, the engagement member 50 of the distal end 14b of the actuator 14 is configured to push the front surface 56b of a respective ramp 56 and slide over the top surface 56a of the ramp 56. In the current illustration, as the actuator 14 radially expands due to heat, the distal end 14b of the actuator 14 moves in a counter-clockwise direction, thus pushing one of the teeth 18 shown in FIG. 10 to the left as indicated by the solid arrow. As the actuator 14 is cooled, the wound member 14 retracts and the distal end 14b of the wound member may simply slide over the top surface 56a of the ramp 56 to the right of the ramp 56 that was pushed. Naturally, as the wound member retracts, at some point the distal end of the wound member 14 is free of all of the ramps 56.

As with the counting unit 10, 10a shown in FIGS. 2, 4, 6 and 7, when the electrical device 100 is removed from the autoclave or allowed to cool down, the actuator 14 is returned to the first configuration. However, unlike the counting unit 10a in FIGS. 6 and 7, the distal end 14b of the wound member 14 is free of and spaced apart from the teeth 18 and instead engages ramps 56 to rotate the rotary member 12. When the electrical device 100 is powered, the first sensor 16 is powered and the microcontroller 32 is able to read the position indicator 28 on the second surface 26 and compare the reading from the position indicator 28 to determine that the position of the rotary member 12 has changed. The microcontroller 32 may be further programmed to associate that change in position with a thermal event and thereby associate the change in position with a thermal event, or a sterilization. Accordingly, the counting unit 10b is able to count the number of times the electrical device 100 has been sterilized.

It should be appreciated that the thermal event that actuates the actuator 14 to change shape from the first configuration to the second configuration is associated with the temperatures generated by an autoclave. Thus, the actuator 14 is formed of a material which does not change shape until the material reaches a temperature associated with autoclaving, such as at least 121 degrees Celsius. As such, the actuator 14 will not be actuated by being merely placed in a hot room or a hot car.

Figure 11:
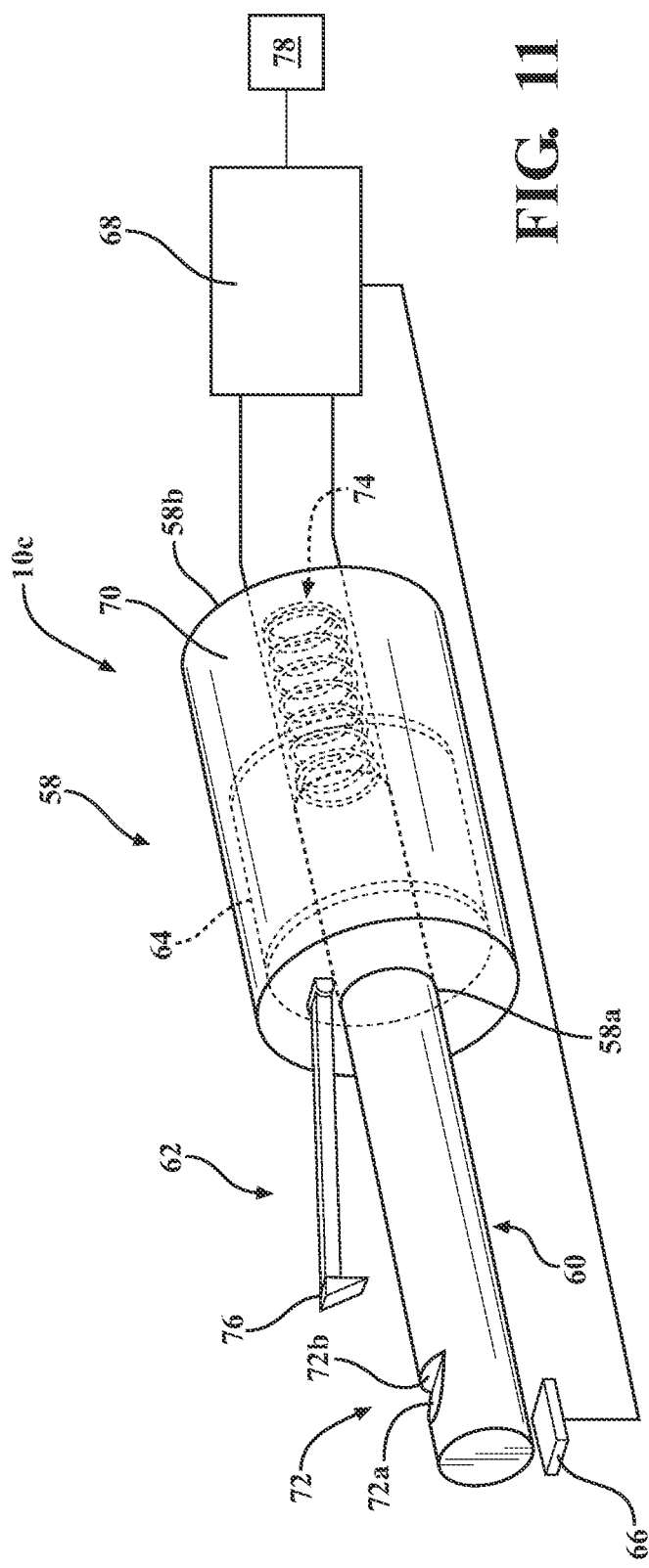
FIG. 11 is a perspective view of a third embodiment of a counting unit view configured for use in the electric device shown in FIG. 1.
Figure 12:
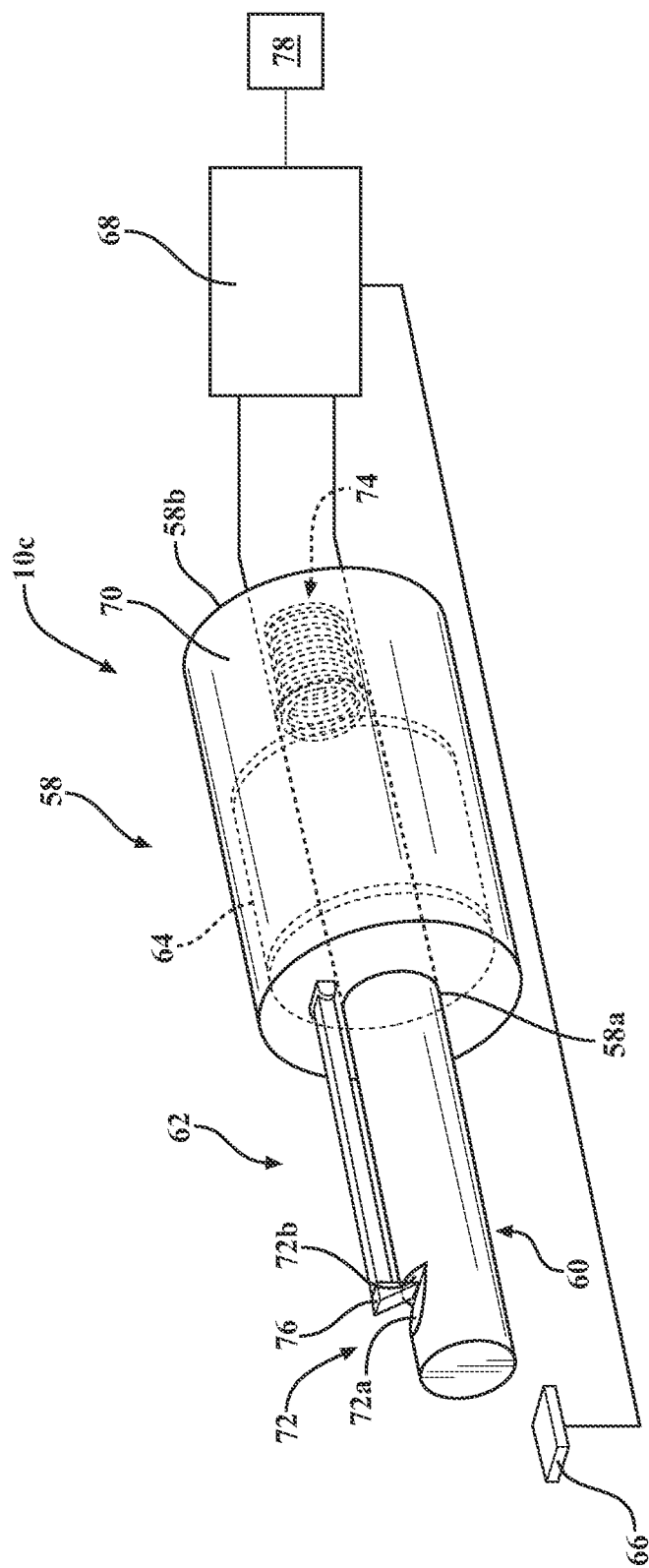
FIG. 12 is a view of the counting unit shown in FIG. 11 showing the plunger in the seated position.

With reference now to FIGS. 11 and 12, a description of a third embodiment of a counting unit 10c for use in an electrical device 100 is provided. The counting unit 10c includes a second housing 58, a plunger 60, a heat responsive arm 62, a drive 64, a second sensor 66, and a controller 68. The counting unit 10c is configured to count a thermal event.

The second housing 58 is illustratively shown as being cylindrical with an open end 58a opposite of a closed end 58b. Preferably, the second housing 58 is formed of a durable material configured to withstand an autoclaving process, such as steel. The second housing 58 includes an interior void 70 for second housing 58 components of the counting unit 10.

The plunger 60 is slidably disposed within the second housing 58. The plunger 60 is a cylindrical member. A portion of the plunger 60 is disposed through the open end 58a of the second housing 58 and a portion of the plunger 60 is disposed within the interior void 70 of the second housing 58. The plunger 60 is moveable from a seated position to an extended position. FIG. 11 shows the plunger 60 in the extended position and FIG. 12 shows the plunger 60 in the seated position.

The plunger 60 includes a second catch 72. The second catch 72 is shown as being a notch which is formed by a slanted surface 72a and a back wall 72b so as to form a generally "V" shaped cross-sectional. The back wall 72b extends along a plane extending radially from a center of the plunger 60 so as to be flat. The second catch 72 is illustratively shown as being disposed adjacent a distal end of the plunger 60; however, it should be appreciated that the second catch 72 may be formed adjacent a center of the plunger 60 or any area in between.

The counting unit 10c further includes a second biasing member 74. The second biasing member 74 is disposed within the second housing 58 between the open end 58a and the closed end 58b. One end of the second biasing member 74 is fixed in an inner surface of the closed end 58b. The second biasing member 74 continuously urges the plunger 60 out of the second housing 58 and into the extended position. The second biasing member 74 is illustratively shown as being a coil spring; however, any biasing member known and used or later developed may be modified for use herein.

The heat responsive arm 62 is disposed on an exterior surface of the open end 58a of the second housing 58 and is generally parallel to and spaced apart from the plunger 60. The heat responsive arm 62 is movable from an engaged position (FIG. 12) and a disengaged position (FIG. 11). The heat responsive arm 62 is configured to move from the engaged to the disengaged position when the heat responsive arm 62 reaches a predetermined temperature. The heat responsive arm 62 is in the engaged position when the heat responsive arm 62 is below the predetermined temperature. The heat responsive arm 62 is formed of a material configured to change shape, such material is known and illustratively includes a shape memory alloy such as Nitinol® or may be a bimetallic material wherein each metal has different heat expansion rates.

FIG. 11 shows the heat responsive arm 62 in the disengaged position. In the engaged position, the heat responsive arm 62 locks the plunger 60 in the seated position. FIG. 12 shows the heat responsive arm 62 in the engaged position. In the disengaged position, the heat responsive arm 62 is disengaged with the plunger 60. The heat responsive arm 62 may include a tab 76 disposed on the distal end of the heat responsive arm 62. The tab 76 is configured to engage the second catch 72 of the plunger 60 so as to prevent the second biasing member 74 from urging the plunger 60 into the extended position.

The drive 64 is disposed within the second housing 58 and is electrically powered. The drive 64 is operable to move the plunger 60 from the extended position to the seated position. In other words, the drive 64 is configured to pull the plunger 60 into the second housing 58. The drive 64 is mechanically configured to generate sufficient pulling force to overcome the force of the second biasing member 74. In one aspect, the drive 64 is a coil of wire that when powered generates an electromagnetic force configured to pull the plunger 60 inwardly into the second housing 58. The controller 68 is further configured to provide electrical power to the drive 64 so as to move the plunger 60 into the extended position when connected to electric power. In one aspect, the controller 68 includes a battery which may be electrically coupled to the electrical device 100. In another aspect, the controller 68 is electrically powered by an electrical connection of the electrical device 100 to a residential or commercial power plug. For example, the counting device may include a power input 78 configured to electrically connect to the power supply of the electrical device, the power input 78 may be a pair of wires which pass through the controller 68. In such an aspect, the controller 68 includes known electrical components (not shown) configured to regulate power to the drive 64. Such known electrical components include but are not limited to relays, fuses and the like.

The second sensor 66 is configured to detect the plunger 60 when the plunger 60 is in the extended position. Any sensor configured to detect the presence of an object may be adapted for use herein, illustratively including an infrared sensor, a photoelectric cell, a capacitive sensor, and the like. In such a manner, the second sensor 66 may detect the presence of the plunger 60 by contact or by proximity. For illustrative purposes, the second sensor 66 is shown displaced from the distal end of the plunger 60 when the plunger 60 is in the extended position. However, it may be the case that the second sensor 66 is a capacitive sensor which is configured to contact the plunger 60 to determine that the plunger 60 is in the extended position. As such, the depiction shown in FIG. 11 is illustrative and not limiting to the scope of the appended claims.

The controller 68 is configured to detect the position of the plunger 60 and count the number of times the drive 64 moves the plunger 60 from the extended position to the seated position. The number of times the plunger 60 moves from the extended to the seated position may be associated with a thermal event so as to track the number of times the electrical device 100 has been sterilized. The controller 68 may be a microcontroller mounted onto a printed circuit board 30 which includes electrical components configured to count the number of times the electrical device 100 has been sterilized. As described above, this may be done by associating a thermal event with a sterilization. The controller 68 may determine a thermal event by counting the number of times the plunger 60 is detected in the extended position or by the number of times the drive 64 draws the plunger 60 from the extended position to the seated position.

In operation, the counting unit 10c is disposed within the electrical device 100 wherein the plunger 60 is in the seated position, as shown in FIG. 12. When the user sterilizes electrical device 100, using an autoclave as an example, the heat responsive arm 62 is moved from engaged position to the disengaged position when the heat responsive arm 62 reaches a predetermined temperature. It should be noted that the predetermined temperature need not be the operating temperature of the autoclave, but may be set to be lower. For instance, the predetermined temperature may be 100 degrees Celsius.

As the heat responsive arm 62 moves from the engaged position to the disengaged position, the tab 76 clears the second catch 72 allowing the second biasing member 74 to urge the plunger 60 from the seated position to the extended position. The plunger 60 remains in the extended position during the duration of the sterilization process. When removed from the autoclave, the electrical device 100 is allowed to cool wherein the heat responsive arm 62 returns to the engaged position. However, the plunger 60 is still in the extended position and thus the tab 76 of the heat responsive arm 62 is not engaged with the second catch 72 but just behind the catch, e.g. disposed between the second catch 72 and the open end 58a of the second housing 58.

When the electrical device 100 is powered, the second sensor 66 is able to detect that the plunger 60 is in the extended position, wherein the controller 68 processes the position of the plunger 60 and powers the drive 64 so as to move the plunger 60 into the seated position. The drive 64 draws the plunger 60 into the second housing 58, overcoming the biasing force of the second biasing member 74 so as to move the second catch 72 past the tab 76, wherein the tab 76 is free to engage the second catch 72. The controller 68 may be configured to turn off the drive 64 when the plunger 60 is in the seated position. In one aspect, the controller 68 is configured to actuate the drive 64 for a predetermined period of time before turning off the drive 64. In such an aspect, the predetermined period of time is sufficient to draw the plunger 60 into the seated position. In another aspect, a third sensor 66a may be positioned within the second housing 58 to detect when the plunger 60 is in the seated position. In either case, when the drive 64 is turned off, the second biasing member 74 is free to urge the plunger 60 from the seated position to the extended position. However, the tab 76 of the heat responsive arm 62 engages the second catch 72 of the plunger 60 so as to retain the plunger 60 in the seated position.

As described above, the controller 68 is configured to count and track the number of sterilizations. In one aspect, the determination of a sterilization is made by a thermal event, which may be associated with the detection of the plunger 60 in the extended position, or the actuation of the drive 64.

It should be appreciated that the thermal event that actuates the heat responsive arm 62 to move from the engaged to the disengaged position is associated with the temperatures generated by an autoclave. Thus, the heat responsive arm 62 is formed of a material which does not change shape until the material reaches a temperature associated with autoclaving, such as at least 121 degrees Celsius. As such, the heat responsive arm 62 will not be actuated by being merely placed in a hot room or a hot car.

A number of implementations have been described. Nevertheless, it will be understood that various modifications may be made without departing from the spirit and scope of the disclosure. For instance, the number of position indicators 28, conductive traces 34, contact pads 36 and teeth 18 are provided for illustrative purposes and the operation of the counting unit 10, 10a, 10b may be performed with fewer or more position indicators 28, conductive traces 34, contact pads 36 and teeth 18 than what is shown. Accordingly, other implementations are within the scope of the following claims.

The invention claimed is:

1. A counting unit for counting a number of times an electrical device has been sterilized, the counting unit comprising:
a rotary member configured to rotate about a first axis, the rotary member including a plurality of position indicators fixedly disposed on the rotary member, the position indicators each including binary encoding;
an actuator configured to engage the rotary member, the actuator configured to change shape from a first configuration to a second configuration when subjected to a predetermined temperature, wherein the actuator engages the rotary member so as to rotate the rotary member when the actuator changes shape from the first configuration to the second configuration; and
a sensor including contact pads in a fixed position and configured to detect a predetermined number of the plurality of position indicators to determine a rotation of the rotary member, the predetermined number of the plurality of position indicators being less than a total number of the plurality of position indicators.

2. The counting unit as set forth in claim 1, wherein the rotary member includes a plurality of teeth, the actuator configured to engage one of the plurality of teeth in the second configuration so as to rotate the rotary member in a first direction.

3. The counting unit as set forth in claim 2, further including a catch configured to rotate about a second axis and configured to engage one of the plurality of teeth so as to prevent the rotary member from rotating in a second direction, the second direction opposite of the first direction.

4. The counting unit as set forth in claim 3, further including a biasing member configured to continuously urge the rotary member in the second direction.

5. The counting unit as set forth in claim 4, wherein the actuator is an elongated member having a proximal end and a distal end, the distal end configured to engage one of the plurality of teeth, and wherein in the first configuration a distance between the proximal end and the distal end is a first length and in the second configuration the distance between the proximal end and the distal end is a second length, a distance between the distal end of the first length and the distal end of the second length is greater than a distance from one of the plurality of teeth to an adjacent one of the plurality of teeth.

6. The counting unit as set forth in claim 1, wherein the actuator is an elongated member in the second configuration.

7. The counting unit as set forth in claim 6, wherein actuator includes a flex portion, wherein the flex portion is configured to straighten the elongated member when the actuator is subjected to the predetermined temperature.

8. The counting unit as set forth in claim 7, wherein a proximal end of the main body portion is fixed to an anchor point.

9. The counting unit as set forth in claim 1, wherein the actuator is an elongated member made of a shape memory alloy.

10. The counting unit as set forth in claim 9, wherein the shape memory alloy is made from one of a copper-aluminum-nickel alloy and a nickel titanium alloy.

11. The counting unit as set forth in claim 1, wherein the actuator is a wound member configured to radially expand when subjected to the predetermined temperature.

12. The counting unit as set forth in claim 11, wherein the wound member is made of a bimetallic material.

13. A counting unit for counting a number of times an electrical device has been sterilized, the counting unit comprising:
a housing having a bore, the bore having a cylindrical shape, the housing having an open end opposite of a closed end, the open end in communication with the bore;
a plunger disposed within the housing, wherein a first portion of the plunger is disposed within the bore and a second portion of the plunger is disposed outside of the bore, the plunger including a catch disposed on the second portion, the plunger moveable from a seated position to an extended position;
a second biasing member disposed within the bore of the housing, the second biasing member disposed between the plunger and the closed end of the housing, the second biasing member continuously urging the plunger out of the housing;

a heat responsive arm movable between an engaged position wherein the heat responsive arm is below a predetermined temperature and locks the plunger in the seated position, and a disengaged position where the heat responsive arm reaches the predetermined temperature and disengages from the plunger;

a drive electrically powered, the drive operable to overcome a force of the second biasing member and move the plunger from the extended position to the seated position;

a sensor configured to detect the plunger when the plunger is in the extended position; and a controller configured to detect and count the number of times the drive moves the plunger from the extended position to the seated position.

14. The counting unit as set forth in claim 13, wherein the drive is a coil of wire.

15. The counting unit as set forth in claim 13, wherein the heat responsive arm is formed of a bimetallic material.

16. The counting unit as set forth in claim 13, further including a power input configured to provide electrical power to the drive so as to move the plunger into the seated position when connected to electric power.

17. The counting unit as set forth in claim 16, wherein the controller is operable to actuate the drive to move the plunger into the seated position when the sensor detects that the plunger is in the extended position.

* * * * *